United States Patent [19]

Gentelia et al.

[11] Patent Number: 5,226,904

[45] Date of Patent: Jul. 13, 1993

[54] ELECTROSURGICAL INSTRUMENT

[75] Inventors: John Gentelia, Madison; Robert Uhl, Manlius; William Wheatley, Utica; Sharyn Longo, Frankfort, all of N.Y.

[73] Assignee: Conmed Corporation, Utica, N.Y.

[21] Appl. No.: 652,632

[22] Filed: Feb. 8, 1991

[51] Int. Cl.[5] .............................................. A61B 17/39
[52] U.S. Cl. .................................... 606/42; 606/45; 606/49; 200/505; 200/510; 200/520
[58] Field of Search ................. 606/41, 42, 45, 48–50; 200/505, 510, 520

[56] References Cited

U.S. PATENT DOCUMENTS

| | | | |
|---|---|---|---|
| 3,801,766 | 4/1974 | Morrison, Jr. | 606/42 X |
| 4,032,738 | 6/1977 | Esty et al. | |
| 4,034,761 | 7/1977 | Prater et al. | 606/42 |
| 4,170,234 | 10/1979 | Graham | 606/42 |
| 4,427,006 | 1/1984 | Nottke | |
| 4,492,832 | 1/1985 | Taylor | |
| 4,545,375 | 10/1985 | Cline | |
| 4,619,258 | 10/1986 | Pool | |
| 4,688,569 | 8/1987 | Rabinowitz | |
| 4,802,476 | 2/1989 | Noerenberg et al. | |
| 4,872,454 | 10/1989 | Deoliveira et al. | |
| 4,911,159 | 3/1990 | Johnson et al. | |
| 4,919,129 | 4/1990 | Weber, Jr. et al. | |
| 4,922,903 | 5/1990 | Welch et al. | |

FOREIGN PATENT DOCUMENTS

0181733 5/1986 European Pat. Off. ............. 606/42

*Primary Examiner*—Lee S. Cohen
*Attorney, Agent, or Firm*—Larson & Taylor

[57] ABSTRACT

A simple and reliable electrosurgical instrument includes a cable having a main contact wire and first second insulated switch wires all provided with a short insulated or bare portion. The cable is received in a main member having a first holding mechanism for holding the switch wires adjacent uninsulated portions thereof on one lateral side and spaced from one another as well as a second holding mechanism for holding the switch wires adjacent the uninsulated portions thereof on the other lateral side so that the uninsulated portions span between the first and second holding mechanisms and are spaced longitudinally from one another. A blade receiver receives an electrode blade and is then electrically connected to the contact wire. A switch device selectively connects one of the uninsulated portions of the switch wires to the contact wire during operation. The first and second holding mechanisms preferably include channels and a cover includes projections which hold the wires in place. The switch device also preferably includes a contact strip which is attached to the distal end to the blade receiver and at a proximal end to the contact wire. This contact strip extends longitudinally and above but immediately adjacent the uninsulated portions of the switch wires. Two respective switches mounted in the cover are then selectively depressed to push the contact strip into engagement with an associated bared switch wire therebeneath. This contact strip includes a U-shaped portion which is resiliently held in contact with the uninsulated portion of the contact wire.

31 Claims, 4 Drawing Sheets

ELECTROSURGICAL INSTRUMENT

FIELD OF THE INVENTION

The present invention relates generally to electrosurgical instruments, and more particularly to a simple, reliable and inexpensive electrosurgical instrument.

BACKGROUND OF THE INVENTION

Electrosurgical instruments are known in the art and are used for electrosurgery. Typically, a suitable electrical generator provides a high frequency or radio frequency signal which is transmitted to a small surgical electrode having a thin knife-like tip which is applied to a patient. The patient is grounded to a patient plate, with the plate being connected by a further conductor back to the generator. The relatively small area of contact by the electrode with the patient provides an intense current in a highly localized area, producing a cutting action. The current then passes through the patient's body to the patient plate wherein the area of contact is large enough that no burning effect occurs at this location.

For cutting purposes, the generator is activated to produce a continuous signal, typically a sine wave signal. However, the same instrument may also be applied to the wound after cutting in order to produce coagulation. This coagulation is produced by a pulsing signal from the generator. Switching means are thus needed for the operator to switch between the two types of electrical energy produced by the generator.

Although a number of arrangements have been devised for selectively activating the electrical energy, the most satisfactory of these arrangements is a multiple wire cable conductor extending from the generator to the electrode. One conductor is normally connected to the electrode to carry the therapeutic current and two other conductors are selectively connectable to the therapeutic current conductor through switches to complete circuits back to the activating means for causing the generator to produce the desired mode of current.

Electrosurgical instruments found to be particularly safe and effective for surgical applications are those which incorporate finger actuated switches, those which allow for readily interchangeable electrodes, those which are water resistant, and those which are thin and properly balanced for close surgical use where a certain "feel" is necessary. Such instruments are typically described as an "electrosurgical pencil." However, such prior instruments have had many disadvantages in that the electrode connections were expensive to achieve, failed to provide a positive connection, and/or were subject to wear problems.

Disclosed in U.S. Pat. No. 4,427,006 (Nottke) is an electrosurgical instrument providing an advantageous interface between an electrosurgical electrode and an electrosurgical generator. In particular, the wires of pins are forced through the insulation of these wires. A conductor plate with specific strips lies over the insert and these strips are selectively connected to the contact pins by use of dome spring push buttons.

In U.S. Pat. No. 4,688,569 (Rabinowitz) a finger actuated surgical electrode holder is disclosed which includes a light transmitting electrode tip. This instrument includes complicated switches having an over-toggle action of spring members as well as a spring element which makes contact with the electrode by a wedging action.

In U.S. Pat. No. 4,545,375 (Kline) an electrosurgical instrument is disclosed which includes an insulated inner core about the main contact wire. The core includes internal switch wires which are actuated outside by deflectable buttons. A split cylindrical member resiliently receives the electrode.

Other U.S. Patents of general interest disclosing electrosurgical instruments include the following: U.S. Pat. No. 4,619,258 (Poole); U.S. Pat. No. 4,872,454 (Duliveria et al.); U.S. Pat. No. 4,492,832 (Taylor); U.S. Pat. No. 4,032,738 (Este et al.); U.S. Pat. No. 4,922,903 (Welch et al.); U.S. Pat. No. 4,802,476 (Nuremberg et al.); U.S. Pat. No. 4,911,159 (Johnson); and U.S. Pat. No. 4,919,129 (Weber, Jr. et al.).

SUMMARY OF THE INVENTION

In accordance with the present invention, a simple and reliable electrosurgical instrument is provided. This instrument provides electrical energy from an electrosurgical generator to a patient for cutting, coagulation, and the like. The instrument includes an electrode blade and a cable which is electrically connected to the electrosurgical generator. This cable includes a main contact wire, and first and second insulated switch wires, each having a short uninsulated or bare portion. The cable is received in a hollow elongate body which includes a main member and a cover. The main member has lateral sides, a first holding means for holding the switch wires adjacent uninsulated portions thereof on one lateral side of the main member and spaced from one another, and a second holding means for holding the switch wires adjacent the uninsulated portions on the other lateral side so that the uninsulated portions span between the first and second holding means and are spaced longitudinally from one another. A blade receiver resiliently receives the electrode blade and is electrically connected to the contact wire to provide electrical connection between the contact wire and the electrode blade. Finally, a switch means is provided for selectively connecting one of the uninsulated portions of the switch wires to the contact wire so that a selected electrical energy is transmitted along the contact wire to the electrode blade from the generator.

In a preferred embodiment the first and second holding means include channels in which respective switch wires are resiliently received. In addition, the cover includes respective projections which project into adjacent channels to maintain the respective switch wires in the respective channels.

In the preferred embodiment, the switch means includes a contact strip which is attached at a distal end to the blade receiver and at a proximal end to the contact wire. This contact strip extends longitudinally and above but immediately adjacent the uninsulated portions of the switch wires. Two respective switches are then mounted in the cover above respective uninsulated portions and are selectively depressed to push the contact strip into engagement with an associated switch wire therebeneath. Preferably, the main member also includes an upstanding ridge, which is located between the first and second holding means and underneath of the contact strip, over which each of the uninsulated portions of the switch wires extend.

The contact strip also includes a U-shaped portion at the proximal end. The main member then includes a slot in which the U-shaped portion is resiliently received.

An uninsulated portion of the contact wire is also preferably received in the slot underneath of the U-shaped portion. A retainer is then provided in the cover which engages the U-shaped portion and maintains the U-shaped portion in this slot and in engagement with the uninsulated portion of the contact wire. The slot also includes a recess formed by a lip in which a free end of the U-shaped portion is also trapped.

In the preferred embodiment, the switches are upstanding buttons of a one-piece elastic pad. Respective apertures are then provided in the cover through which these buttons project. A retainer member is also attached to the cover to maintain the pad in place sealingly with the cover. In addition, the main member further includes a bridge between the uninsulated portions of the switch wires and which extends above them. The elastic pad then also includes a projection which presses an underlying portion of the contact strip into abutment with this bridge.

The blade receiver for the electrode includes a contact member. The main member then includes a nose in which the contact member is integrally molded to seal the contact member from a remainder of the main member. The blade member also includes a contact tail which extends out of the nose of the main member and beneath the cover. This contact tail is inwardly wedge-shaped, and the contact strip then has a distal end provided with an elongate hole. When the contact tail is received through the elongate hole, the contact strip is rotated 90° with respect to the contact tail to trap the contact strip between the nose of the main member and the contact tail and thus to force the slot to spread and form a cold weld between the contact strip and the contact tail.

It is an advantage of the present invention that a very cost effective manufacturing process is utilizable with the present invention.

It is also an advantage of the present invention that an electrosurgical instrument having improved safety and reliability is produced.

It is a further advantage of the present invention that an electrosurgical instrument is produced having a limited number of parts which are easily assembled.

It is still another advantage of the present invention that the assembly of the electrosurgical instrument of the present invention requires no soldering, welding, or crimping.

Still another advantage of the present invention is that the electrosurgical instrument is completely sealed to fluid entry.

Yet another advantage of the present invention is that there are only two flexing parts, the one-piece pad and the contact strip.

Other features and advantages of the present invention are stated in or apparent from a detailed description of presently preferred embodiments of the invention found hereinbelow.

DETAILED DESCRIPTION OF THE PREFERRED EMBODIMENTS

Figure 1:
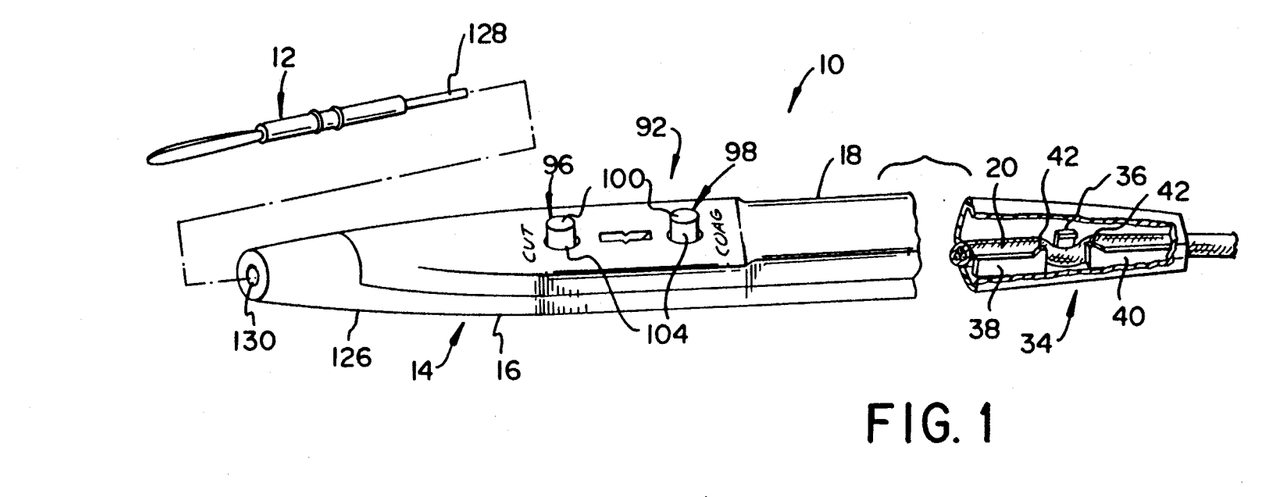
FIG. 1 is a schematic perspective view with portions removed of an electrosurgical pencil in accordance with the present invention.

With reference now to the drawings in which like numerals represent like elements throughout the views, an electrosurgical instrument or pencil 10 is depicted in FIG. 1. Preferably, electrosurgical instrument 10 includes a changeable electrode blade 12, a hollow elongate body 14 including a main member 16 and a cover 18, and a cable 20. As typical of such devices in the art, cable 20 is connected to an electrosurgical generator and includes a main insulated contact wire 22, and first and second insulated switch wires 24 and 26.

The hollow interior of hollow body 14 is completely sealed to fluid entry for safety. Thus, cover 18 is preferably ultrasonically welded to main member 16 at all abutting surfaces after assembly. However, it should be appreciated that cable 20 extends rearwardly from electrosurgical instrument 10 through an aperture 28 in cover 18. To seal this aperture 28, at the rear of main member 16, a block 30 having a semicircular recess 32 therein receives cable 20. Cable 20 is resiliently deformed against semicircular recess 32 by aperture 28 of cover 18 which is complimentarily shaped. Thus, the resilient deformation of cable 20 between block 30 and the remainder of cover 18 forming aperture 28 forms a fluid tight seal around aperture 28.

It should also be appreciated that the fluid tight seal of cable 20 in aperture 28 is separate from a strain relief means 34 provided in hollow body 14. As shown in FIG. 1, cable 20 is bent adjacent a stud 36 provided laterally opposite a gap between walls 38 and 40 along which cable 20 passes. This bending of cable 20 about stud 36 acts as a frictional holding mechanism to provide strain relief when cable 20 is pulled from electrosurgical instrument 10. It should also be noted that walls 38 and 40 include upwardly extending tips 42 to help ease the insertion of cable 20 around stud 36 during assembly. Thereafter, cable 20 is trapped between wall 38 and a wall 39.

Contact wire 22 is designed to make direct electrical contact with electrode blade 12. This connection includes a flexible metal contact strip 44 according to the present invention. Contact strip 44 extends along and above an upstanding ridge 46 provided along main member 16 as shown best in FIG. 2. It should be appreciated that only the two ends of contact strip 44 have been depicted in FIG. 2, with the straight middle portion removed for clarity.

Figure 4:
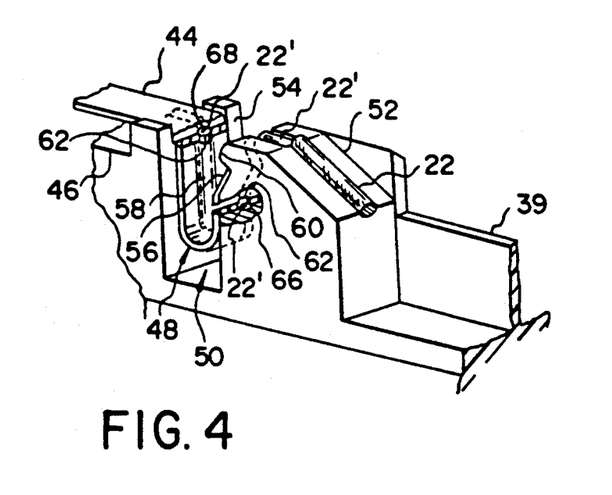
FIG. 4 is a schematic perspective view of the circled portion of FIG. 2 identified with numeral 4.
Figure 4A:
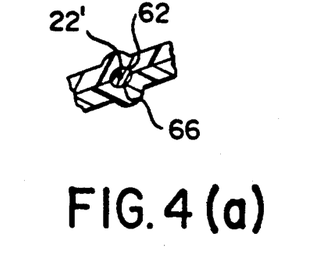

In order to connect contact wire 2 to contact strip 44, the proximal end of contact strip 44 includes a U-shaped portion 48 as best depicted in FIG. 4. U-shaped portion 48 is received in a slot 50 provided between a ramp 52 and a slotted end 54 of upstanding ridge 46. U-shaped portion 48 includes a free end 56 which is trapped in a recess 58 provided by a lip 60 in ramp 52. All of U-shaped portion 48 except for the tip of free end 56 includes a channel 62 on the underside thereof as shown best in the broken out portion.

Figure 2:
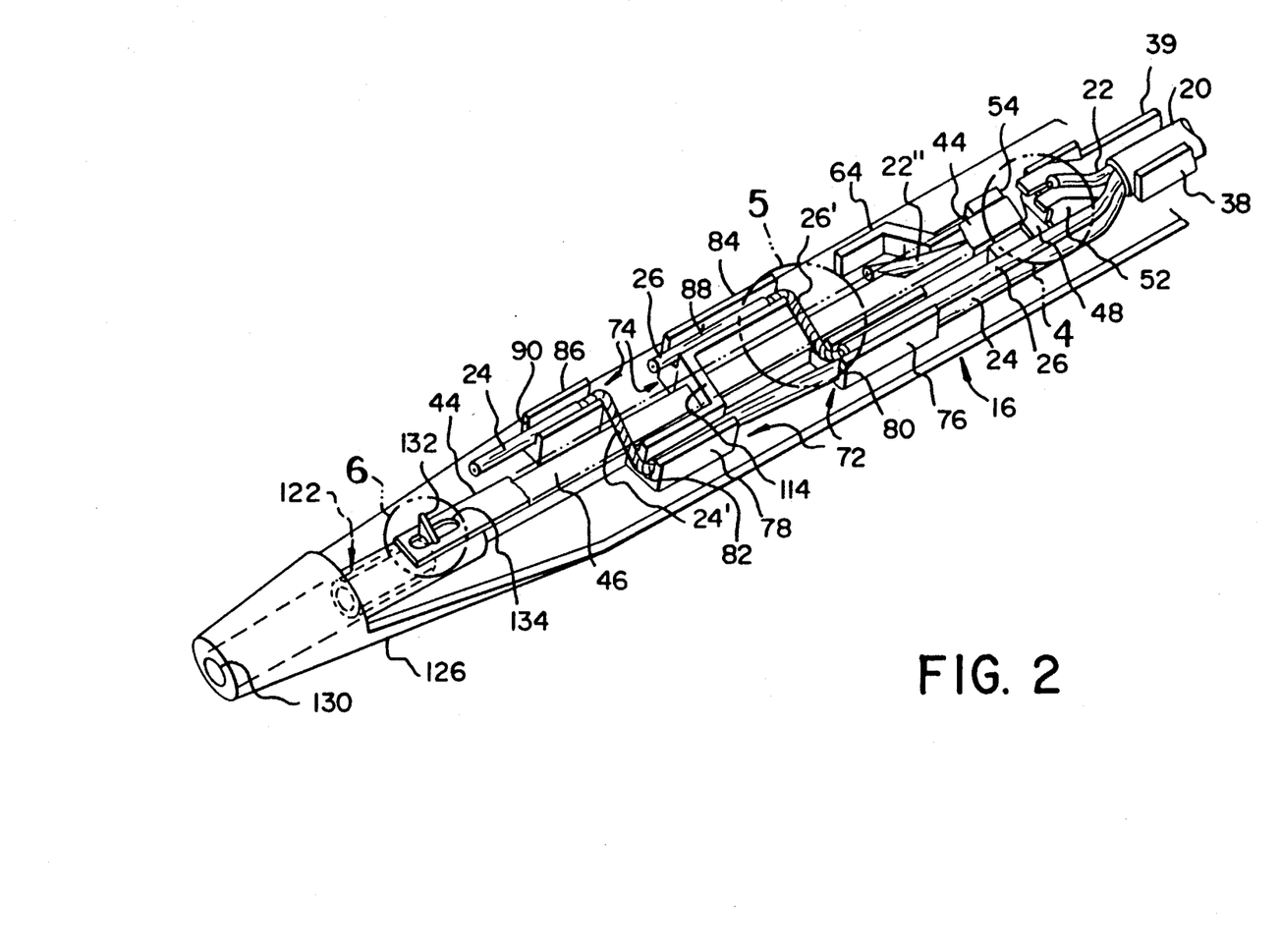
FIG. 2 is a schematic perspective view of a portion of a main member of the electrosurgical pencil depicted in FIG. 1 with the cover removed.
Figure 3:
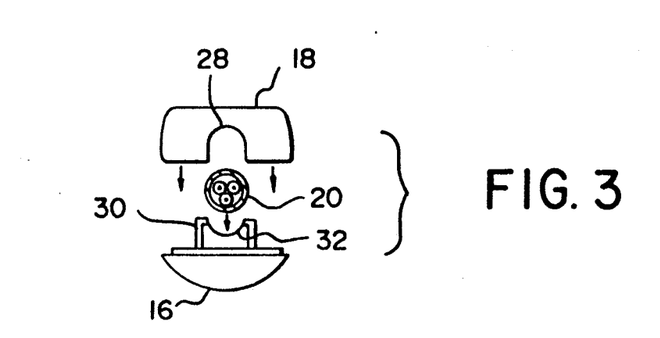
FIG. 3 is a rear elevation view of the instrument depicted in FIG. 1.

In order for U-shaped portion 48 of contact strip 44 to make electrical contact with contact wire 22, contact wire 22 exits from the insulation forming cable 20 just prior to ramp 52 and then is provided with an uninsulated or bare portion 22'. As shown in FIG. 4, uninsulated portion 22' of contact wire 22 is located beneath U-shaped portion 48 of contact strip 44 and is partially located in channel 62. It should be appreciated that a free remainder 22" of contact wire 22 is designed to retain its insulation and remainder 22" is then located between upstanding ridge 46 and a wall 64 as shown in FIG. 2. It should also be appreciated that both ramp 52 and slotted end 54 of upstanding ridge 46 also include corresponding respective channels 66 and 68 in which uninsulated portion 22' of contact wire 22 is partially received.

Figure 7:
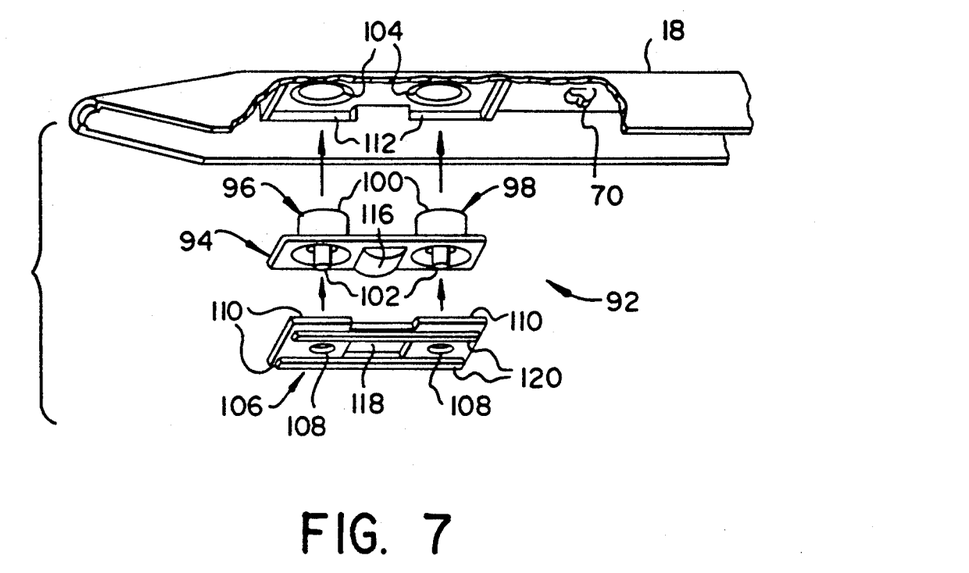
FIG. 7 is a schematic perspective view of a portion of the cover depicted in FIG. 1 showing the connection of the buttons.

When U-shaped portion 48 of contact strip 44 is pushed into slot 50 after placement of uninsulated portion 22' of contact wire 22 in channels 66 and 68 is achieved, U-shaped portion 48 makes electrical contact with uninsulated portion 22' along the length thereof as uninsulated portion 22' is also received in channel 62 of U-shaped portion 48. This electrical contact is further assured by leaving the tip of free end 56 without a channel 62 so that a flat surface meets uninsulated portion 22' thereat as free end 56 is trapped beneath lip 60 in recess 58. Further, as shown in FIG. 7, cover 18 includes a retainer 70 which is sized to project into slot 50 and maintain U-shaped portion 48 pressed against uninsulated portion 22' of contact wire 22. U-Shaped portion 48 is thus under spring tension toward underlying uninsulated portion 22' of contact wire 22. Further, retainer 70 not only insures that U-shaped portion 48 remains in slot 50, but also causes free end 56 to dig into uninsulated portion 22' of contact wire 22 beneath lip 60. This action forms a cold weld and provides an extremely good electrical contact.

As shown in FIG. 2, both first switch wire 24 and second switch wire 26 exit from the insulation of cable 20 just prior to ramp 52 and pass around one side thereof. Switch wires 24 and 26 then are received in respective first holding means 72 and second holding means 74. First holding means 72 includes blocks 76 and 78 which are located on one side of upstanding ridge 46. Block 76 includes a channel 80 therein which resiliently receives insulated portions of both switch wires 24 and 26. Block 78 also includes a channel 82 which is sized to resiliently receive an insulated portion of first switch wire 24. On the other side of upstanding ridge 46, second holding means 74 includes blocks 84 and 86 having channels 88 and 90 therein which are sized to resiliently receive an insulated portion of respective switch wires 26 and 24.

Figure 5:
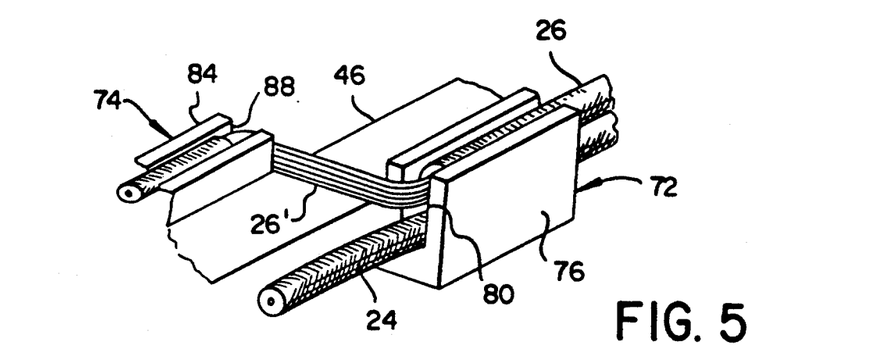
FIG. 5 is an enlarged perspective view of the circled portion of the main member depicted in FIG. 2 identified with the numeral 5.

Conveniently, blocks 76, 78, 84, and 86 are integrally molded with the rest of hollow body 14 and particularly with upstanding ridge 46. It should also be appreciated that both switch wires 24 and 26 include uninsulated or bare portions 24' and 26'. Both uninsulated portions 24' and 26' are located along the lengths of switch wires 24 and 26 so that uninsulated portions 24' and 26' span between first and second holding means 72 and 74 and on top of upstanding ridge 46 as shown best in FIG. 5 for second switch wire 26.

As shown in greater detail in FIG. 7, electrosurgical instrument 10 includes a switch means 92 which selectively makes contact between one of uninsulated portions 24' or 26' of switch wires 24 and 26 and contact strip 44 (which is electrically connected to uninsulated portion 22' of contact wire 22). Switch means 92 includes a one-piece elastic pad 94 which forms two switches 96 and 98. Switches 96 and 98 include buttons 100 and associated tips 102. Buttons 100 project upwardly through apertures 104 provided in cover 18. Elastic pad 94 is held in position with buttons 100 projecting through apertures 104 in cover member 18. Retainer member 106 includes apertures 108 through which tips 102 extend and retainer member is provided with flanges 110. Cover 18 is then provided with corresponding recesses 112 for reception of flanges 110. Therefore, it will be appreciated that one-piece elastic pad 94 is retained in cover 18 by a snap fit of flanges 110 of retainer member 106 into recesses 112. It will be further appreciated that this snap fit of retainer member 106 and cover 18 supplies sufficient force against elastic pad 94 to seal the periphery of elastic pad 94 to cover 18, thus making a fluid tight seal for buttons 100.

Elastic pad 94 is sized and spaced so that tips 102 overly a respective uninsulated portion 24' or 26' of switch wires 24 and 26. Thus, when one of buttons 100 is depressed, the associated tip 102 presses a portion of contact strip 44 into electrical contact with the associated uninsulated portion 24' or 26' of switch wires 24 and 26. In this embodiment, switch wire 24 causes a cutting current to be provided to electrode blade 12 when contacted with contact strip 44 and thus switch 96 has been labelled "CUT" on cover 18 as shown in FIG. 1. Similarly, switch 98 has been labelled "COAG" to indicate that a coagulating current is provided when switch 98 is depressed to make electrical contact between switch wire 26 and contact strip 44.

In order to assure that only one of uninsulated portions 24' or 26' of switch wires 24 and 26 are contacted by depression of an associated button 100, a bridge 114 is integrally formed with upstanding ridge 46 and extends between blocks 78 and 84 as shown in FIG. 2. Bridge 114 is thus located midway between uninsulated portions 24' and 26' and is taller than uninsulated portions 24' and 26'. In addition, as shown in FIG. 7, elastic pad 94 includes a projection 116 which extends downwardly through a central window 118 of retainer member 106. Projection 116 is sized to resiliently press an underlying portion of contact strip 44 into contact with bridge 114 at all times. Thus, it will be appreciated that when one of buttons 100 is depressed causing tip 102 to push an underlying portion of contact strip 44 into engagement with the underlying uninsulated portion 24' or 26', the portion of contact strip 44 on the other side of bridge 114 tends to be raised and thus further removed from contact with the other uninsulated portion 24' or 26'.

As shown best in FIG. 7, retainer member 106 also includes elongate tongues 120 on either lateral side thereof. Tongues 120 are sized and positioned to be received in channels 80, 82, 88, and 90 of respective blocks 76, 78, 84, and 86 when cover 18 is in place to assure that respective switch wires 24 and 26 are retained in place.

Figure 6:
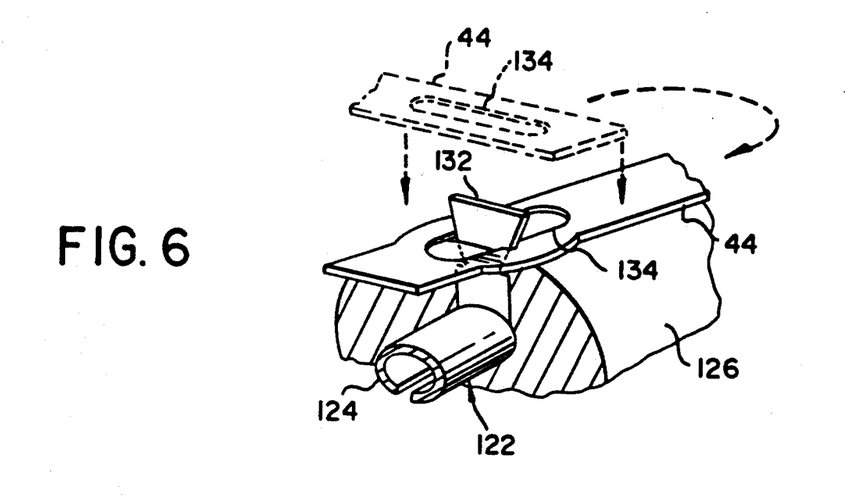
FIG. 6 is a schematic perspective view with portions cut away of the circled portion in FIG. 2 identified with the numeral 6 and showing the connection of the contact strip to the contact tail.

Electrosurgical instrument 10 also includes a blade receiver 122 which resiliently receives electrode blade 12 and which is electrically connected to contact wire 22. As shown in FIG. 6, blade receiver 122 includes a contact member 124 in the form of a split cylindrical metal piece. Contact member 124 is integrally molded in a nose 126 of main member 16 in order to hold and seal contact member 124 therein. Contact member 124 resiliently receives a cylindrical plug 128 of electrode blade 112 through an elongate bore 130 provided in nose 126.

In order to provide electrical contact between blade receiver 122 sealed in nose 126 and contact strip 44, blade receiver 122 further includes a contact tail 132. As shown in FIGS. 2 and 6, contact tail 132 is inwardly (toward contact member 124) wedge shaped and extends upwardly from contact member 126 through nose 126 into the hollow interior of hollow body 14. Nose 126 is integrally molded about contact tail 132 as well as contact member 124 in order to provide a fluid tight seal about blade receiver 122. Thus, it will be appreciated that no fluid can pass from elongate bore 130 into the hollow interior of hollow body 14.

As best shown in FIG. 6, contact strip 44 includes an elongate hole 134 at the distal end thereof. Elongate hole 134 is sized to receive contact tail 132 therethrough as shown by the portion of contact strip 44 shown in broken lines in FIG. 6 and the downwardly directed arrows. Thereafter, contact strip 44 is rotated 90° as shown by the curved arrow to the position depicted in full lines in FIG. 6. This rotation causes a cold weld to be provided between contact tail 132 and contact strip 44 as contact strip 44 is trapped between nose 126 and the inward wedge shape of contact member 124. A slight spreading of elongate hole 134 is also achieved, assuring a good electrical contact between contact strip 44 and contact tail 132.

Figure 8:
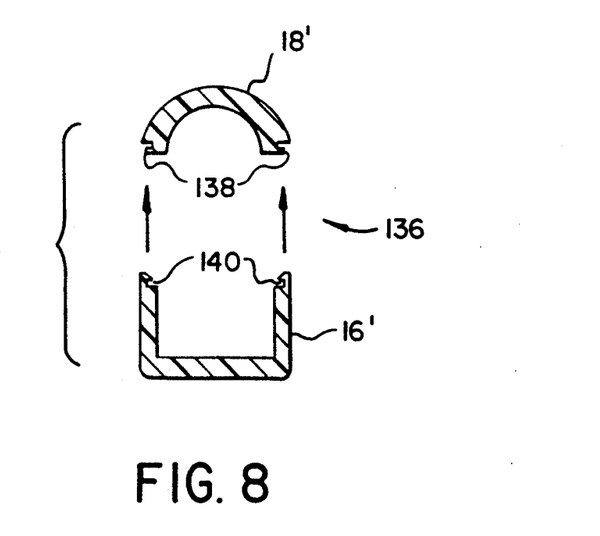
FIG. 8 is a cross-sectional view of an alternative connection scheme between the cover and main member.

In order to provide a fluid tight seal for hollow body 14, cover 18 is closely mated to main member 16. As indicated above, a sonic weld along the mating surfaces thereof then completes the sealing of the hollow interior of hollow body 14. However, as an alternative, a snap together seal means 136 as depicted in FIG. 8 can be utilized. As shown, snap together means 136 includes a stepped edge 138 of a cover 18' and a corresponding ramped/stepped edge 140 of a main member 16'.

Electrosurgical instrument 10 as described above allows for a very cost effective manufacturing process while improving both safety and reliability of instrument 10. It will initially be appreciated that electrosurgical instrument 10 is comprised of only 7 elements (excluding interchangeable electrode blades 12): cover 18, retainer member 106, keypad 94, integrally molded main member 16, blade receiver 122, contact strip 44, and cable 20. These elements are easily assembled, requiring no soldering, welding, or crimping. Further, this easy assembly is accomplished at a single station, assembly is not complex, and during assembly everything is completely visible.

It will also be appreciated that electrosurgical instrument 10 is completely sealed to fluid entry for safety. In particular, blade receiver 122 is integrally insert molded in nose 126, one-piece elastic pad 94 acts as its own gasket, the rear seal between aperture 28 and block 30 is effective and does not form part of a strain relief for cable 20, and main member 16 is ultrasonically welded with cover 18 (in one embodiment) and this is done at a position below (away from) wires 22, 24, and 26 as well as all other contacts and exposed metal parts which might be harmed by such welding.

It will further be appreciated that electrosurgical instrument 10 has a durable and reliable design. Only two flexing parts are present in instrument 10, elastic pad 94 and contact strip 44. Both of these elements are particularly suited for repeated flexing without fatigue.

While electrosurgical instrument 10 has been described as using an interchangeable electrode blade 12, it should be appreciated that a fixed blade would also be possible. Further, while electrode blade 12 has been depicted with an insulated portion in the center thereof, electrode blade 12 could also be uninsulated and the same protection provided by extending nose 126.

It will further be appreciated that the switch means is very simple and makes use of a direct contact to an uninsulated or bare portion of the wires which make up cable 20. If desired, these uninsulated or bare portions can be tinned. The use of uninsulated or bare portions between insulated portions is also advantageous because it keeps the ends of wires 22, 24, and 26 from fraying as well as providing body to move these wires into the respective receiving channels. Wires 24 and 26 are then held in place in the channels by tongues 120 as mentioned above.

The ease of assembly of the present invention is also enhanced by the configuration of both elastic pad 94 and retainer member 106. Neither of these elements are direction sensitive, so that they can be oriented in either direction during assembly. Simplicity is also enhanced because tactile feel of buttons 100 is determined by the web thickness of elastic pad 94 and the derometer of the material. As mentioned above, elastic pad 94 is self-sealing. In addition, if a rocker switch (not shown) is installed in the slot between buttons 100, elastic pad 94 also serves as a seal for this member.

Besides being easy to assemble, electrosurgical instrument 10 is also easily tested both mechanically and electrically during assembly. This can be done just prior to the attaching of cover 18 to main member 16, and allows any needed repairs to be made before the final assembly of cover 18 to main member 16. This is particularly advantageous because there are no hidden assemblies or complex electrical contacts. The provision of properly spaced uninsulated portions 22', 24', and 26' also assures their proper placement as one cannot be misplaced without the uninsulated portion obviously being out of place or causing other uninsulated portions to be out of place.

While the present invention has been described with respect to exemplary embodiments thereof, it will be understood by those of ordinary skill in the art that variations and modifications can be effected within the scope and spirit of the invention.

We claim:

1. A simple and reliable electrosurgical instrument for selectively providing electrical energy from an electrosurgical generator to a patient for cutting, coagulation, and the like comprising:
   an electrode blade;
   a cable adapted to be connected to the electrosurgical generator, said cable including a main contact wire, and first and second insulated switch wires each having a short uninsulated portion;
   a hollow elongate body including a main member and a cover, said main member including (a) lateral sides, (b) a first holding means for holding said switch wires adjacent said uninsulated portions on one lateral side of said main member and spaced from one another, and (c) a second holding means for holding said switch wires adjacent said uninsulated portions on the other lateral side whereby said uninsulated portions span between said first and second holding means and are spaced longitudinally from one another;

a blade receiver within the elongate body which resiliently receives said electrode blade and which is electrically connected to said contact wire to provide electrical connection between said contact wire and said electrode blade, said electrode blade extending from the elongate body; and a switch means for selectively connecting one of said uninsulated portions of said switch wires to said contact wire such that a selected electrical energy is transmitted along said contact wire to said electrode blade from the generator.

2. An electrosurgical instrument as claimed in claim 1 wherein said first and second holding means include channels in which respective said switch wires are resiliently received.

3. An electrosurgical instrument as claimed in claim 2 wherein said cover includes respective projections which project into adjacent said channels to maintain respective said switch wires in respective said channels.

4. An electrosurgical instrument as claimed in claim 3 wherein said switch means includes (a) a contact strip which is attached at a distal end to said blade receiver and at a proximal end to said contact wire, said contact strip extending longitudinally and above but immediately adjacent said uninsulated portions of said switch wires, and (b) two switches mounted in said cover above respective said uninsulated portions of said switch wires which are selectively depressed to push said contact strip into engagement with an associated said switch wire.

5. An electrosurgical instrument as claimed in claim 4 wherein said proximal end of said contact strip includes a U-shaped portion, and wherein said main member includes a slot in which said U-shaped portion is resiliently received.

6. An electrosurgical instrument as claimed in claim 5 wherein said contact wire includes an uninsulated portion which is received in said slot underneath said U-shaped portion; and wherein said cover includes a retainer which engages said U-shaped portion and maintains said U-shaped portion in said slot and in engagement with said uninsulated portion of said contact wire.

7. An electrosurgical instrument as claimed in claim 6 wherein said switches are upstanding buttons of a one-piece elastic pad; wherein respective apertures are provided in said cover through which said buttons project; and wherein a retainer member is attached to said cover to maintain said pad in place sealingly with said cover and said projections are provided on said retainer.

8. An electrosurgical instrument as claimed in claim 7 wherein said blade receiver includes a contact tail extending out of said main member and beneath said cover, said contact tail being inwardly wedge shaped; and wherein said distal end of said contact strip is provided with an elongate hole therein whereby said contact tail is received through said elongate hole and said contact strip is rotated 90° with respect to said contact tail to trap said contact strip between said main member and said contact tail and force said slot to spread and form a cold weld between said contact strip and said contact tail.

9. An electrosurgical instrument as claimed in claim 8 wherein said main member includes a bridge between said uninsulated portions of said switch wires which extends above said uninsulated portions; and wherein said elastic pad includes a projection which presses an underlying portion of said contact strip into abutment with said bridge.

10. An electrosurgical instrument as claimed in claim 1 wherein said switch means includes (a) a contact strip which is attached at a distal end to said blade receiver and at a proximal end to said contact wire, said contact strip extending longitudinally and above but immediately adjacent said uninsulated portions of said switch wires, and (b) two switches mounted in said cover above respective said uninsulated portions of said switch wires which are selectively depressed to push said contact strip into engagement with an associated said switch wire.

11. An electrosurgical instrument as claimed in claim 10 wherein said main member includes an upstanding ridge, located between said first and second holding means and underneath said contact strip, over which each of said uninsulated portions of said switch wires extend.

12. An electrosurgical instrument as claimed in claim 10 wherein said proximal end of said contact strip includes a U-shaped portion, and wherein said main member includes a slot in which said U-shaped portion is resiliently received.

13. An electrosurgical instrument as claimed in claim 12 wherein said contact wire includes an uninsulated portion which is received in said slot underneath said U-shaped portion; and wherein said cover includes a retainer which engages said U-shaped portion and maintains said U-shaped portion in said slot and in engagement with said uninsulated portion of said contact wire.

14. An electrosurgical instrument as claimed in claim 12 wherein said U-shaped portion includes a free end; and wherein said slot includes a recess formed by a lip in which said free end is trapped.

15. An electrosurgical instrument as claimed in claim 10 wherein said switches are upstanding buttons of a one-piece elastic pad; wherein respective apertures are provided in said cover through which said buttons project; and wherein a retainer member is attached to said cover to maintain said pad in place sealingly with said cover.

16. An electrosurgical instrument as claimed in claim 15 wherein said main member includes a bridge between said uninsulated portions of said switch wires which extends above said uninsulated portions; and wherein said elastic pad includes a projection which presses an underlying portion of said contact strip into abutment with said bridge.

17. An electrosurgical instrument as claimed in claim 10 wherein said blade receiver includes a contact tail extending out of said main member and beneath said cover, said contact tail being inwardly wedge shaped; and wherein said distal end of said contact strip is provided with an elongate hole therein whereby said contact tail is received through said elongate hole and said contact strip is rotated 90° with respect to said contact tail to trap said contact strip between said main member and said contact tail and force said slot to spread and form a cold weld between said contact strip and said contact tail.

18. An electrosurgical instrument as claimed in claim 1 wherein said blade receiver includes a contact member; and wherein said main member includes a nose in which said contact member is integrally molded to seal said contact member from a remainder of said main member.

19. An electrosurgical instrument as claimed in claim 18 wherein said blade receiver includes a contact tail extending out of said nose of said main member and beneath said cover, said contact tail being inwardly wedge shaped; and wherein said switch means includes a contact strip having a distal end provided with an elongate hole therein whereby said contact tail is received through said elongate hole and said contact strip is rotated 90° with respect to said contact tail main member and said contact tail and force said slot to spread and form a cold weld between said contact strip and said contact tail.

20. An electrosurgical instrument as claimed in claim 1 wherein said blade receiver includes a contact tail extending out of said main member and beneath said cover, said contact tail being inwardly wedge shaped; and wherein said switch means includes a contact strip having a distal end provided with an elongate hole therein whereby said contact tail is received through said elongate hole and said contact strip is rotated 90° with respect to said contact tail to trap said contact strip between said main member and said contact tail and force said slot to spread and form a cold weld between said contact strip and said contact tail.

21. A simple and reliable electrosurgical instrument for selectively providing electrical energy from an electrosurgical generator to a patient for cutting, coagulation, and the like comprising:
   an electrode blade;
   a cable adapted to be connected to the electrosurgical generator, said cable including a main contact wire, and first and second insulated switch wires each having a short uninsulated portion;
   a hollow elongate body including a main member and a cover, said main member including a holding means for holding said uninsulated portions of said switch wires in a laterally extending position across said main member and spaced from one another;
   a blade receiver within the elongate body which resiliently receives said electrode blade and which is electrically connected to said contact wire to provide electrical connection between said contact wire and said electrode blade, said electrode blade extending from the elongate body; and
   a switch means for selectively connecting one of said uninsulated portions of said switch wires to said contact wire such that a selected electrical energy is transmitted along said contact wire to said electrode blade from the generator, said switch means including (a) a contact strip which is attached at a distal end to said blade receiver and at a proximal end to said contact wire, said contact strip extending longitudinally and above but immediately adjacent said uninsulated portions of said switch wires, said proximal end of said contact strip including a U-shaped portion, and wherein said main member includes a slot in which said U-shaped portion is resiliently received; and (b) two switches mounted in said cover above respective said uninsulated portions of said switch wires and said contact strip which are selectively depressed to push said contact strip into engagement with an associated said switch wire.

22. An electrosurgical instrument as claimed in claim 21 wherein said switches are upstanding buttons of a one-piece elastic pad; wherein respective apertures are provided in said cover through which said buttons project; and wherein a retainer member is attached to said cover to maintain said pad in place sealingly with said cover.

23. An electrosurgical instrument as claimed in claim 22 and further including a bridge between said uninsulated portions of said switch wires which extends above said uninsulated portions; and wherein said elastic pad includes a projection which presses an underlying portion of said contact strip into abutment with said bridge.

24. An electrosurgical instrument as claimed in claim 22 wherein said blade receiver includes a contact tail extending out of said main member and beneath said cover, said contact tail being inwardly wedge shaped; and wherein contact strip of said switch means includes a distal end provided with an elongate hole therein whereby said contact tail is received through said elongate hole and said contact strip is rotated 90° with respect to said contact tail to trap said contact strip between said main member and said contact tail and force said slot to spread and form a cold weld between said contact strip and said contact tail.

25. A simple and reliable electrosurgical instrument for selectively providing electrical energy from an electrosurgical generator to a patient for cutting, coagulation, and the like comprising:
   an electrode blade;
   a cable adapted to be connected to the electrosurgical generator, said cable including a main contact wire, and first and second insulated switch wires;
   a hollow elongate body including a hollow interior and a nose having an elongate bore extending longitudinally of said body, said bore being open at a distal end thereof and closed otherwise by said nose whereby said bore is fluidly isolated from said hollow interior;
   a blade receiver located in said bore which resiliently receives said electrode blade inserted into said distal end of said bore, said blade extending from said elongate body, said blade receiver including a contact tail which extends through said nose and which is electrically connected to said contact wire to provide electrical connection between said contact wire and said electrode blade, said blade receiver further including a cylindrical contact member which is integrally formed with said contact tail; and wherein said contact member and said contact tail are integrally molded in said nose;
   a switch means for selectively connecting one of said switch wires to said contact wire such that a selected electrical energy is transmitted along said contact wire to said electrode blade from the generator.

26. An electrosurgical instrument as claimed in claim 25 wherein said contact tail is inwardly wedge shaped; and wherein said switch means includes a contact strip having a distal end provided with an elongate hole therein whereby said contact tail is received through said elongate hole and said contact strip is rotated 90° with respect to said contact tail to trap said contact strip between said main member and said contact tail and force said slot to spread and form a cold weld between said contact strip and said contact tail.

27. An electrosurgical instrument as claimed in claim 26 wherein said hollow elongate body further includes an upstanding ridge in said hollow interior located parallel but spaced from said contact strip; and a holding means for holding uninsulated portions of said switch wires in a laterally extending position over said upstanding ridge in said hollow interior and spaced from one another and said contact strip.

28. An electrosurgical instrument as claimed in claim 27, wherein said hollow body includes a cover for said hollow interior; wherein said switch means includes two buttons of a one-piece elastic pad; wherein respective apertures are provided in said cover through which said buttons project; and wherein a retainer member is attached to said cover to maintain said pad in place sealingly with said cover.

29. An electrosurgical instrument as claimed in claim 28 wherein said upstanding ridge includes a bridge between said uninsulated portions of said switch wires which extends above said uninsulated portions; and wherein said elastic pad includes a projection which presses an underlying portion of said contact strip into abutment with said bridge.

30. An electrosurgical instrument as claimed in claim 29, wherein a proximal end of said contact strip includes a U-shaped portion; and wherein said elongate body includes a slot in which said U-shaped portion is resiliently received.

31. An electrosurgical instrument as claimed in claim 30 wherein said contact wire includes an uninsulated portion which is received in said slot underneath said U-shaped portion; and wherein said cover includes a retainer which engages said U-shaped portion and maintains said U-shaped portion in said slot and in engagement with said uninsulated portion of said contact wire.

* * * * *